United States Patent [19]

Böhner et al.

[11] Patent Number: 4,990,176

[45] Date of Patent: * Feb. 5, 1991

[54] 4-METHYLTETRAHYDROPHTHALIMIDE HERBICIDES

[75] Inventors: Beat Böhner, Binningen; Hans Moser, Magden, both of Switzerland; Georg Pissiotas, Lörrach, Fed. Rep. of Germany

[73] Assignee: Ciba-Geigy Corporation, Ardsley, N.Y.

[ * ] Notice: The portion of the term of this patent subsequent to Jul. 10, 2007 has been disclaimed.

[21] Appl. No.: 826,428

[22] Filed: Oct. 28, 1988

Related U.S. Application Data

[63] Continuation-in-part of Ser. No. 88,638, Aug. 24, 1987, abandoned.

[30] Foreign Application Priority Data

Sep. 3, 1986 [CH] Switzerland ..................... 3537/86

[51] Int. Cl.$^5$ ..................... A01N 43/38; C07D 209/48
[52] U.S. Cl. ........................ 71/96; 548/513; 564/440; 564/442
[58] Field of Search ............. 548/513; 71/96

[56] References Cited

U.S. PATENT DOCUMENTS

| | | | |
|---|---|---|---|
| 4,431,822 | 2/1984 | Nagano | 548/513 |
| 4,439,229 | 3/1984 | Swithenbank | 71/94 |
| 4,484,940 | 11/1984 | Nagano | 548/513 |
| 4,484,941 | 11/1984 | Nagano | 548/513 |
| 4,594,099 | 6/1986 | Yamada | 71/96 |

FOREIGN PATENT DOCUMENTS

| | | | |
|---|---|---|---|
| 61741 | 10/1982 | European Pat. Off. | |
| 2046754 | 11/1980 | United Kingdom | 548/513 |

OTHER PUBLICATIONS

Yamada I Chem. Abs. 96, 199517j (1981).
Kasugai, Chem. Abs. 81, 34561w (1983).

*Primary Examiner*—Mark L. Berch
*Attorney, Agent, or Firm*—Kevin T. Mansfield; Edward McC. Roberts

[57] ABSTRACT

The invention relates to novel 4-methyltetrahydrophthalimides of the formula I

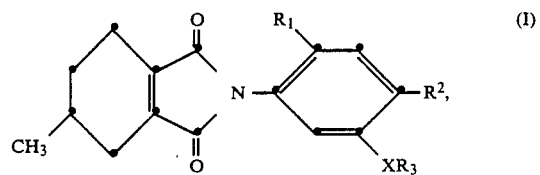

in which the substituents $R_1$, $R_2$, $R_3$ and X have the meanings explained in the text, to processes for their preparation, and to novel selective herbicidal compositions containing compounds of the formula I.

5 Claims, No Drawings

4-METHYLTETRAHYDROPHTHALIMIDE HERBICIDES

The present invention relates to novel derivatives of N-phenyltetrahydrophthalimide having herbicidal and plant growth regulating action, to agrochemical compositions that contain these substances as active ingredients, to the use of the novel N-phenyltetrahydrophthalimides for the selective control of weeds, and to processes for preparation of these novel compounds. The invention relates also to novel intermediates that are used for the preparation of the novel active ingredients.

Herbicidally active N-phenyltetrahydrophthalic acid imides are known from EP-A 61741. These compounds, which are substituted inter alia in the phenylimide moiety by 2,4-dihalo-5-alkoxy, do not, however, contain a methyl substituent in the tetrahydrophthalic acid radical. An individual compound that may be mentioned is N-[4-chloro-2-fluoro-5-propoxyphenyl]-tetrahydrophthalic acid imide. The phthalimides known from the prior art exhibit good herbicidal action per se but have a low degree of selectivity.

Surprisingly, it has now been found that compounds of the formula I are highly effective herbicidally while having good selectivity and being well tolerated by cultivated plants.

The novel N-phenyltetrahydrophthalimide derivatives correspond to the formula I

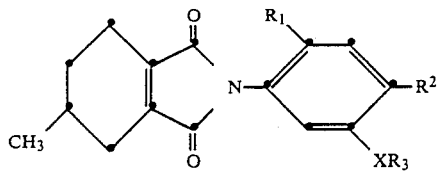

in which
$R_1$ represents hydrogen or fluorine,
$R_2$ represents halogen,
X represents O or S,
$R_3$ represents $C_3$–$C_{10}$-alkenyl; $C_5$–$C_6$-cycloalkyl; $C_5$–$C_6$-cycloalkenyl; $C_3$–$C_{10}$-alkynyl; or $C_1$–$C_{10}$-alkyl which, if desired, is mono- or poly-substituted by halogen, $C_1$–$C_4$-alkoxy, $C_1$–$C_4$-alkoxycarbonyl, cyano, $C_1$–$C_4$alkylthio or by $C_1$–$C_4$-alkylthiocarbonyl.

The 4-methyltetrahydrophthalimides of the formula I are asymmetrically substituted at the $C_4$ ring carbon atom carrying the methyl group and accordingly can be in the R- or in the S-configuration (formula R-I or S-I respectively).

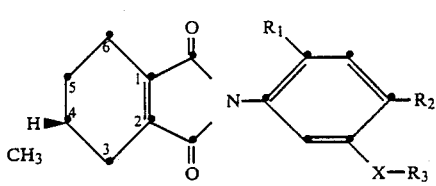

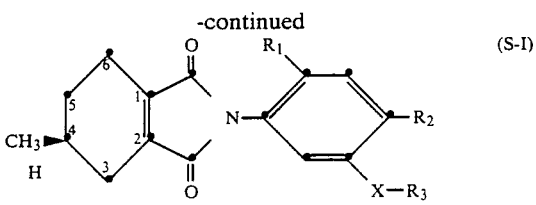

The invention includes both enantiomeric forms and any mixtures thereof, and the racemate.

$C_3$–$C_{10}$-alkenyl radicals are the monounsaturated or, for $C_4$ and above, also polyunsaturated, cis-trans- and also structurally isomeric radicals; such as, for example, the allyl, but-2-en-1-yl or 2-methylprop-2-enyl radical.

$C_5$–$C_6$-cycloalkenyl radicals are cyclopentenyl or cyclohexenyl.

$C_5$–$C_6$-cycloalkyl radicals are cyclopentyl and cyclohexyl.

$C_3$–$C_{10}$-alkynyl radicals are the monounsaturated or, for $C_4$ and above, also polyunsaturated radicals; such as, for example, the propargyl or but-2-ynyl radical.

$C_1$–$C_{10}$-alkyl is methyl, ethyl, propyl, isopropyl, n-butyl, isobutyl, tert.-butyl, sec.-butyl, and the isomeric pentyls, such as n-pentyl, i-pentyl (1-ethylpropyl), t-pentyl (1,1-dimethylpropyl), and the isomeric hexyl, heptyl, octyl, nonyl and decyl radicals.

Halogen is fluorine, chlorine, bromine and iodine, preferably fluorine, chlorine and bromine.

In the other substituents, which are produced by the combination of individual constituent parts, the constituent parts have the meanings selected within the scope of the definition and can be freely selected by combining individual constituents from the above list. In these cases too, this list does not represent a limitation of the invention; it is merely illustrative.

Preferred compounds of the formula I are those in which
$R_1$ represents hydrogen or fluorine,
$R_2$ represents fluorine, chlorine or bromine,
X represents O or S,
$R_3$ represents $C_3$–$C_5$-alkenyl; $C_3$–$C_5$-alkynyl; cyclopentenyl; cyclohexenyl; $C_5$–$C_6$-cycloalkyl; or $C_1$–$C_6$-alkyl which, if desired, is mono-substituted by $C_1$–$C_4$-alkoxy, $C_1$–$C_4$-alkoxycarbonyl, $C_1$–$C_4$-alkylthio, $C_1$–$C_4$-alkylthiocarbonyl or by cyano or is mono- or poly-substituted by identical or different substituents selected from fluorine, chlorine and bromine.

Of the compounds of the formula I described as being preferred, the following individual groups may be mentioned:

Group A:
Compounds of the formula I in which $R_3$ represents methyl, ethyl, isopropyl, n-propyl, n-butyl, sec.-butyl, isobutyl, tert.-butyl, n-pentyl, isopentyl or tert.-pentyl.

Group B:
Compounds of the formula I in which $R_3$ represents allyl, 2-methylpropenyl or but-2-en-1-yl.

Group C:
Compounds of the formula I in which $R_3$ represents propargyl or but-2-ynyl.

Group D:
Compounds of the formula I in which $R_3$ represents cyclopentyl, cyclohexyl, cyclopentenyl or cyclohexenyl.

Group E:

Compounds of the formula I in which $R_3$ represents $C_1$-$C_3$-alkoxycarbonylmethyl or $C_1$-$C_3$-alkoxycarbonylethyl.

Group F:

Compounds of the formula I in which X represents oxygen.

Group G:

Compounds of the formula I in which X represents sulphur.

Group H:

Compounds of the formula I in which $R_1$ represents hydrogen and $R_2$ represents chlorine or bromine.

Group I:

Compounds of the formula I in which $R_1$ represents fluorine and $R_2$ represents chlorine or bromine.

As individual compounds that are especially preferred there may be mentioned:

N-(4-chloro-2-fluoro-5-isopropoxyphenyl)-4-methyl-3,4,5,6-tetrahydrophthalimide, N-(4-chloro-2-fluoro-5-methoxyphenyl)-4-methyl-3,4,5,6-tetrahydrophthalimide, N-[4-chloro-2-fluoro-5-(methoxycarbonylmethyl)-phenyl]-4-methyl-3,4,5,6-tetrahydrophthalimide, N-(4-chloro-2-fluoro-5-isobutoxyphenyl)-4-methyl-3,4,5,6-tetrahydrophthalimide, N-(4-chloro-2-fluoro-5-n-butoxyphenyl)-4-methyl-3,4,5,6-tetrahydrophthalimide, N-(4-chloro-5-ethoxy-2-fluorophenyl)-4-methyl-3,4,5,6-tetrahydrophthalimide.

The compounds of the formula I are prepared according to the invention as follows:

(a) 4-methyl-3,4,5,6-tetrahydrophthalic acid anhydride II is condensed with an aniline of the formula III,

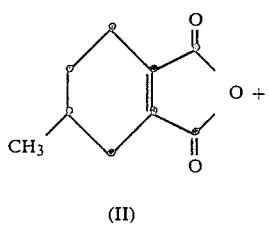

(II)

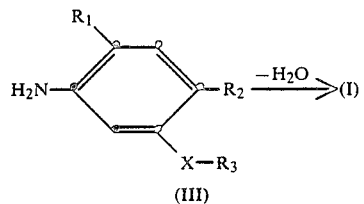

(III)

in which $R_1$, $R_2$, $R_3$ and X have the meanings given under formula I, or (b) a phenol or thiophenol of the formula IV is reacted with a compound of the formula V,

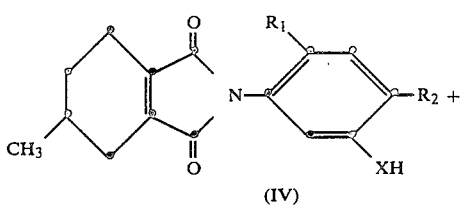

(IV)

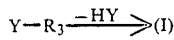

(V)

in which $R_1$, $R_2$, $R_3$ and X have the meanings given under formula I and Y represents a group that can be replaced under the reaction conditions, such as halogen, preferably chlorine, bromine or iodine, or represents a phenylsulphonyl radical which, if desired, is alkylated or halogenated in the phenyl nucleus, or represents a radical of the formula $R_3OSO_2$—O.

The above condensation reactions are advantageously carried out in an inert organic solvent. The reaction temperature is generally from room temperature to the boiling temperature of the reaction mixture, the reaction mixture preferably being heated to reflux. Condensation reaction (a) can be accelerated by the addition of condensation catalysts and by removal of the resulting reaction product, water. A similar effect is obtained by the addition of water-removing agents, such as, for example, sulphuric acid.

Catalysts that come into consideration, especially when an aprotic solvent is used, are: p-toluenesulphonic acid, benzoic acid, 4-dimethylaminopyridine, sulphuric acid, hydrochloric acid or naphthalenesulphonic acid. Reaction procedures of the type mentioned above are customarily used when preparing carboxylic acid derivatives. They correspond to general laboratory practice.

Reaction (b) is advantageously carried out with the addition of bases. Suitable bases are inter alia sodium, potassium and calcium hydroxide, alkali metal and alkaline earth metal carbonates, amines, such as, for example, triethylamine or heterocycles, such as pyridine, DABCO, etc. The reaction can also advantageously be carried out under phase transfer conditions in two-phase systems. Such reactions are familiar to the person skilled in the art (and are described, for example, in Dehmlow and Dehmlow, Phase Transfer Catalysis; Verlag Chemie; Weinheim 1983).

As solvents there are suitable especially higher boiling hydrocarbons, lower alkanecarboxylic acids and their esters and amides, higher boiling ketones and ethers. Examples thereof are benzene, toluene, xylene, dimethylformamide, dimethylacetamide, acetic acid, ethyl acetate, diisopropyl ether, ethylene glycol dimethyl ether, tetrahydrofuran, dioxan, 2-butanone and methyl propyl ketone.

The 4-methyltetrahydrophthalic acid anhydride II used as starting compound is known in the literature (Beilstein, Handbuch der Organ. Chemie, Vol. $17^{III/IV}$, p. 6003). This compound can be prepared in an especially advantageous manner by acid-catalysed isomerisation of 4-methyl-1,2,3,6-tetrahydrophthalic acid anhydride according to processes known in the literature (Chem. Abs. 78 71559 k).

The anilines of the formula III are novel in part. They can be prepared according to processes known per se:

(a) by reduction of nitro compounds of the formula VI

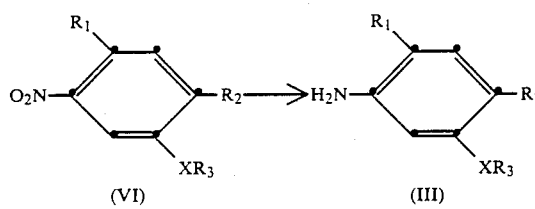

for example by catalytic processes (such as H₂/Pd/C, H₂/Pt, etc.), or (b) by reaction of a phenol or thiophenol of the formula VII with a compound of the formula V

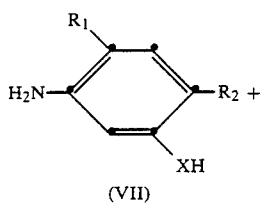

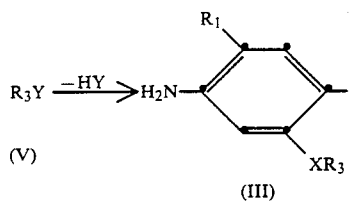

if desired with the addition of bases.

In the formulae (III), (V), (VI) and (VII) the radicals R₁, R₂, R₃ and X have the meanings given for formula I. Y represents a group that can be replaced under the reaction conditions, such as halogen, preferably chlorine, bromine or iodine, or represents a phenylsulphonyl radical which, if desired, is alkylated or halogenated in the phenyl nucleus, or represents a radical of the formula R₃—O—SO₂—O.

The invention relates also to the novel compounds of the formula IV

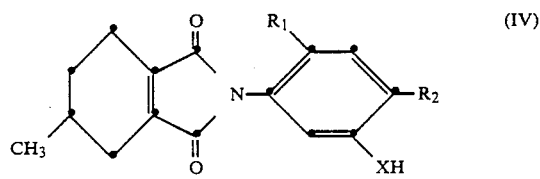

in which

R₁ represents hydrogen or fluorine,

R₂ represents halogen, and

X represents O or S.

Compounds of the formula IV in which R₂ represents fluorine, chlorine or bromine are preferred.

The compounds of the formula IV can be obtained by reaction of 4-methyl-3,4,5,6-tetrahydrophthalic acid anhydride II with an aniline of the formula VII

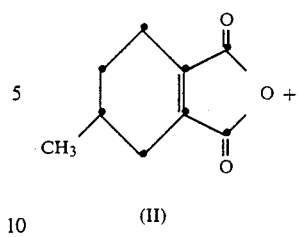

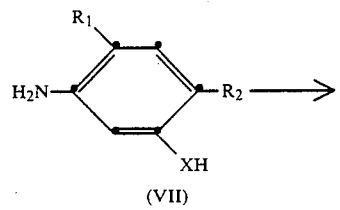

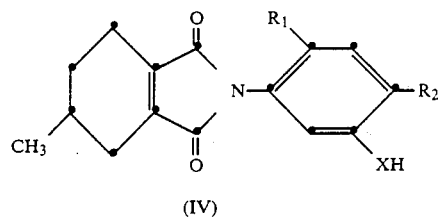

R₁ represents hydrogen or fluorine,

R₂ represents halogen, and

X represents O or S.

The process can be carried out analogously to process (a) described above for the manufacture of compounds of the formula I.

The compounds of the formula I are highly active plant active ingredients which, at suitable application rates, have excellent suitability as selective herbicides for the control of weeds in crops of useful plants. That is to say, at these application rates the active ingredients of the formula I are distinguished by the property of a good selective herbicidal action against weeds. Cultivated plants, such as rye, barley, oats, wheat, maize, millet, rice, cotton and soya, remain virtually undamaged at low application rates. When application rates are increased, the growth of the cultivated plants is affected only slightly. If very high application rates are used, the substances of the formula I exhibit total-herbicidal properties.

The compounds of formula I can advantageously be used as defoliation or desiccation agents especially in cotton.

The selective herbicidal action of the compounds according to the invention is observed in both pre-emergence and post-emergence use. These active ingredients can therefore be used with equally good results in a pre-emergence method and in a post-emergence method for the selective control of weeds.

The invention relates also to herbicidal compositions that contain a novel active ingredient of the formula I and to methods for the pre-emergence and post-emergence control of weeds.

The compounds of the formula I are used in unmodified form or, preferably, in the form of compositions together with the adjuvants customary in formulation technology, and are therefore processed in known manner, for example, to form emulsifiable concentrates, directly sprayable or dilutable solutions, dilute emulsions, wettable powders, soluble powders, dusts, granulates, and also encapsulations in, for example, polymeric substances. As with the nature of the compositions, the methods of application, such as spraying, atomising, dusting, scattering or pouring, are chosen in accordance with the intended objectives and the given circumstances.

The formulations, that is to say the agents, preparations or compositions containing the active ingredient of the formula I and, where appropriate, a solid or liquid adjuvant, are prepared in known manner, for example by intimate mixing and/or grinding of the active ingredients with extenders, such as, for example, solvents, solid carriers and, where appropriate, surface-active compounds (surfactants).

As solvents there may be suitable: aromatic hydrocarbons, preferably having from 8 to 12 carbon atoms, such as, for example, xylene mixtures or substituted naphthalenes, phthalic acid esters, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethylformamide, and, where appropriate, epoxidised vegetable oils, such as epoxidised coconut oil or soybean oil, or water.

As solid carriers, for example for dusts and dispersible powders, there are generally used natural mineral powders, such as calcite, talcum, kaolin, montmorillonite or attapulgite. In order to improve the physical properties it is also possible to add highly disperse silicic acid or highly disperse absorbent polymers. As granulated adsorbent carriers there come into consideration porous types, such as, for example, pumice, broken brick, sepiolite or bentonite, and as non-sorbent carrier materials, for example, calcite or sand. Furthermore, a large number of pre-granulated materials of inorganic or organic character can be used, such as, especially, dolomite or pulverised plant residues.

Depending upon the nature of the active ingredient of the formula I to be formulated, as surface-active compounds there come into consideration non-ionic, cationic and/or anionic surfactants having good emulsifying, dispersing and wetting properties. Surfactants are to be understood as meaning also mixtures of surfactants.

Suitable anionic surfactants can be both so-called water-soluble soaps and water-soluble synthetic surface-active compounds.

As soaps there may be mentioned alkali metal, alkaline earth metal or optionally substituted ammonium salts of higher fatty acids ($C_{10}$-$C_{22}$), such as, for example, the sodium or potassium salts of oleic or stearic acid, or of mixtures of natural fatty acids that can be obtained, for example, from coconut oil or tallow oil. Fatty acid methyltaurine salts should also be mentioned.

More frequently, however, so-called synthetic surfactants are used, especially fatty sulphonates, fatty sulphates, sulphonated benzimidazole derivatives or alkylarylsulphonates.

The fatty sulphonates or sulphates are generally in the form of alkali metal, alkaline earth metal or optionally substituted ammonium salts and contain an alkyl radical having from 8 to 22 carbon atoms, alkyl also including the alkyl moiety of acyl radicals, for example the sodium or calcium salt of ligninsulphonic acid, of dodecylsulphuric acid ester or of a mixture of fatty alcohol sulphates produced from natural fatty acids.

Also included are the salts of sulphuric acid esters and sulphonic acids of fatty alcohol/ethylene oxide adducts. The sulphonated benzimidazole derivatives preferably contain 2 sulphonic acid groups and a fatty acid radical having from 8 to 22 carbon atoms. Alkylarylsulphonates are, for example, the sodium, calcium or triethanolamine salts of dodecylbenzene sulphonic acid, of dibutylnaphthalenesulphonic acid or of a naphthalenesulphonic acid/formaldehyde condensation product.

There also come into consideration corresponding phosphates, such as, for example, salts of the phosphoric acid ester of a p-nonylphenol-(4–14)ethylene oxide adduct, or phospholipids.

As non-ionic surfactants there come into consideration especially polyglycol ether derivatives of aliphatic or cycloaliphatic alcohols, saturated or unsaturated fatty acids and alkylphenols, which derivatives may contain from 3 to 10 glycol ether groups and from 8 to 20 carbon atoms in the (aliphatic) hydrocarbon radical and from 6 to 18 carbon atoms in the alkyl radical of the alkylphenols.

Further suitable non-ionic surfactants are the water-soluble adducts of polyethylene oxide with polypropylene glycol, ethylenediaminopolypropylene glycol and alkylpolypropylene glycol having from 1 to 10 carbon atoms in the alkyl chain, which adducts contain from 20 to 250 ethylene glycol ether groups and from 10 to 100 propylene glycol ether groups, the mentioned compounds customarily containing from 1 to 5 ethylene glycol units per propylene glycol unit.

As examples of non-ionic surfactants there may be mentioned nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, also come into consideration.

The cationic surfactants are especially quaternary ammonium salts that contain, as N-substituent, at least one alkyl radical having from 8 to 22 carbon atoms and, as further substituents, lower, optionally halogenated alkyl, benzyl or lower hydroxyalkyl radicals. The salts are preferably in the form of halides, methylsulphates or ethylsulphates, for example stearyltrimethylammonium chloride or benzyldi-(2-chloroethyl)-ethylammonium bromide.

The surfactants customarily used in formulation technology are described inter alia in the following publications: "1986 International McCutcheon's Emulsifiers & Detergents", Glen Rock, N.J., U.S.A.; H. Stache, "Tensid-Taschenbuch", 2nd Edition, C. Hanser Verlag, Munich, Vienna, 1981; M. and J. Ash. "Encyclopaedia of Surfactants", Vol. I–III, Chemical Publishing Co., New York, 1980–1981.

The active ingredient preparations generally contain from 0.1 to 95%, especially from 0.1 to 80%, active ingredient of the formula I, from 1 to 99.9% of one or more solid or liquid adjuvants and from 0 to 25% of a surfactant.

The preferred formulations have especially the following compositions: (%=percent by weight)
Emulsifiable concentrates:
active ingredient: 1 to 20%, preferably 5 to 10%
surface-active agents: 5 to 30%, preferably 10 to 20% liquid carriers: 50 to 94%, preferably 70 to 85%
Dusts:
active ingredient: 0.1 to 10%, preferably 0.1 to 1%
solid carrier: 99.9 to 90%, preferably 99.9 to 99%
Suspension concentrates:
active ingredient: 5 to 75%, preferably 10 to 50%
water: 94 to 25%, preferably 88 to 30%
surface-active agent: 1 to 40%, preferably 2 to 30%
Wettable powder:
active ingredient: 0.5 to 90%, preferably 1 to 80%
surface-active agent: 0.5 to 20%, preferably 1 to 15%
solid carrier: 5 to 95%, preferably 15 to 90%
Granulates:
active ingredient: 0.5 to 30%, preferably 3 to 15%
solid carrier: 99.5 to 70%, preferably 97 to 85%

Whilst concentrated formulations are preferred as commercial products, the end user generally uses dilute formulations. The forms of application can be diluted down to 0.001% active ingredient. The application rates are generally from 0.001 to 4 kg active ingredient/ha, preferably from 0.005 to 1 kg active ingredient/ha.

The compositions may also contain further adjuvants, such as stabilizers, anti-foam agents, viscosity regulartors, binders, tackifiers and fertilizers, or other active ingredients, in order to obtain specific effects.

EXAMPLE 1

Preparation examples

Example 1a

Preparation of N-(4-chloro-2-fluoro-5-isopropoxyphenyl)-4-methyl-3,4,5,6-tetrahydrophthalic acid imide 45.0 g (0.27 mol) of 4-methyl-3,4,5,6-tetrahydrophthalic acid anhydride are dissolved in 300 ml of toluene. 54.2 g (0.27 mol) of 2-fluoro-4-chloro-5-isopropoxyaniline and 0.5 g of dimethylaminopyridine are added and the mixture is heated until the solvent and the water that has formed distil off. After approximately 2 hours at a bath temperature of 145° C. the reaction is complete. The residue is chromatographed over a silica gel column with hexane/ethyl acetate 9:1.

75.3 g (79.3%) of the title compound of the formula

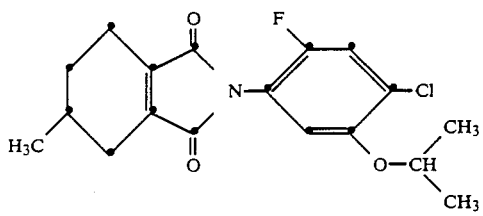

are isolated in the form of colourless crystals having a melting point of 88°–89° C. (Compound No. 1.031).

Example 1b

Preparatiion of N-(4-chloro-5-ethoxy-2-fluorophenyl)-4-methyl-3,4,5,6-tetrahydrophthalic acid imide 6.1 g (0.02 mol) of N-(2-fluoro-4-chloro-5-hydroxyphenyl)-4-methyl-3,4,5,6-tetrahydrophthalic acid imide are heated at 80° C. together with 3.0 g (0.022 mol) of potassium carbonate in 50 ml of methyl propyl ketone. After 30 minutes a thick salt is precipitated. 1.95 ml (0.024 mol) of ethyl iodide are added at 40° C. and the reaction mixture, which is now thinly liquid again, is stirred for 2 hours at 45° C. in order to complete the reaction. After filtration, the filtrate is concentrated by evaporation and the oil that remains is recrystallised from ether/hexane.

5.6 g (83.6%) of the title compound of the formula

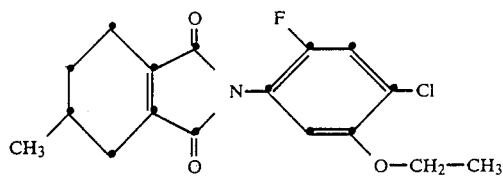

are isolated in the form of pale beige crystals having a melting point of 108°–109° C. (Compound No. 1.029).

The following compounds of the formula I

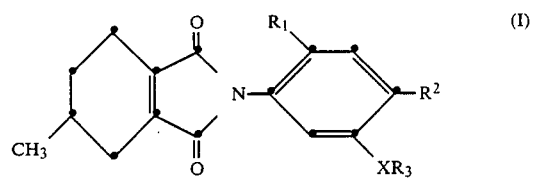

can be obtained analogously to Examples 1a and 1b.

| Comp. No. | $R_1$ | $R_2$ | X | $R_3$ | physical data |
|---|---|---|---|---|---|
| 1.001 | H | Cl | O | $CH_3$ | |
| 1.002 | H | Cl | O | $C_2H_5$ | |
| 1.003 | H | Cl | O | $n-C_3H_7$ | |
| 1.004 | H | Cl | O | $i-C_3H_7$ | |
| 1.005 | H | Cl | O | $n-C_4H_9$ | |
| 1.006 | H | Cl | O | $i-C_4H_9$ | |
| 1.007 | H | Cl | O | $s-C_4H_9$ | |
| 1.008 | H | Cl | O | $t-C_4H_9$ | |
| 1.009 | H | Cl | O | $n-C_5H_{11}$ | |
| 1.010 | H | Cl | O | $i-C_5H_{11}$ | |
| 1.011 | H | CL | O | cyclopentyl | |
| 1.012 | H | Cl | O | cyclohexyl | |
| 1.013 | H | Cl | O | $CH_2-CH=CH_2$ | |
| 1.014 | H | Cl | O | $CH_2-C(CH_3)=CH_2$ | |
| 1.015 | H | Cl | O | $CH_2-CH=CH-CH_3$ | |
| 1.016 | H | Cl | O | $CH_2-C\equiv CH$ | |
| 1.017 | H | Cl | O | $CH_2-C\equiv C-CH_3$ | |
| 1.018 | H | Br | O | $CH_3$ | |
| 1.019 | H | Br | O | $C_2H_5$ | |
| 1.020 | H | Br | O | $n-C_3H_7$ | |
| 1.021 | H | Br | O | $i-C_3H_7$ | |
| 1.022 | H | Br | O | $n-C_4H_9$ | |
| 1.023 | H | Br | O | $i-C_4H_9$ | |
| 1.024 | H | Br | O | $n-C_6H_{13}$ | |
| 1.025 | H | Br | O | $CH_2-CH=CH_2$ | |
| 1.026 | H | Br | O | $CH_2-CH=CH-CH_3$ | |
| 1.027 | H | Br | O | $CH_2-C\equiv CH$ | |
| 1.028 | F | Cl | O | $CH_3$ | M.p.=111–112° C. |
| 1.029 | F | Cl | O | $C_2H_5$ | M.p.=108–109° C. |
| 1.030 | F | Cl | O | $n-C_3H_7$ | |
| 1.031 | F | Cl | O | $i-C_3H_7$ | M.p.=88–89° C. |
| 1.032 | F | Cl | O | $n-C_4H_9$ | $n_D^{21}=1.3905$ |
| 1.033 | F | Cl | O | $i-C_4H_9$ | M.p.=93–95° C. |
| 1.034 | F | Cl | O | $s-C_4H_9$ | |
| 1.035 | F | Cl | O | $t-C_4H_9$ | |
| 1.036 | F | Cl | O | $n-C_5H_{11}$ | |
| 1.037 | F | Cl | O | $i-C_5H_{11}$ | |
| 1.038 | F | Cl | O | cyclopentyl | |
| 1.039 | F | Cl | O | cyclohexyl | |
| 1.040 | F | Cl | O | $n-C_6H_{13}$ | |
| 1.041 | F | Cl | O | $CH_2-CH=CH_2$ | |

-continued

| Comp. No. | $R_1$ | $R_2$ | X | $R_3$ | physical data |
|---|---|---|---|---|---|
| 1.042 | F | Cl | O | $CH_2-C(CH_3)=CH_2$ | |
| 1.043 | F | Cl | O | $CH_2-CH=CH-CH_3$ | |
| 1.044 | F | Cl | O | $CH_2-C\equiv CH$ | |
| 1.045 | F | Cl | O | $CH_2-C\equiv C-CH_3$ | |
| 1.046 | F | Cl | O | cyclopropyl (as drawn) | |
| 1.047 | F | Cl | O | cyclohexenyl (as drawn) | |
| 1.048 | F | Cl | O | $CH_2-COOCH_3$ | M.p.=101–102° C. |
| 1.049 | F | Br | O | $CH_3$ | |
| 1.050 | F | Br | O | $C_2H_5$ | |
| 1.051 | F | Br | O | $n-C_3H_7$ | |
| 1.052 | F | Br | O | $i-C_3H_7$ | |
| 1.053 | F | Br | O | $n-C_4H_9$ | |
| 1.054 | F | Br | O | $i-C_4H_9$ | |
| 1.055 | F | Br | O | $s-C_4H_9$ | |
| 1.056 | F | Br | O | $t-C_4H_9$ | |
| 1.057 | F | Br | O | $n-C_5H_{11}$ | |
| 1.058 | F | Br | O | $i-C_5H_{11}$ | |
| 1.059 | F | Br | O | cyclopentyl | |
| 1.060 | F | Br | O | cyclohexyl | |
| 1.061 | F | Br | O | $n-C_6H_{13}$ | |
| 1.062 | F | Br | O | $CH_2-CH=CH_2$ | |
| 1.063 | F | Br | O | $CH_2-C(CH_3)=CH_2$ | |
| 1.064 | F | Br | O | $CH_2-CH=CH-CH_3$ | |
| 1.065 | F | Br | O | $CH_2-C\equiv CH$ | |
| 1.066 | F | Br | O | $CH_2-C\equiv C-CH_3$ | |
| 1.067 | F | Br | O | cyclopropyl (as drawn) | |
| 1.068 | F | Br | O | cyclohexenyl (as drawn) | |
| 1.069 | H | Cl | S | $CH_3$ | |
| 1.070 | H | Cl | S | $C_2H_5$ | |
| 1.071 | H | Cl | S | $n-C_3H_7$ | |
| 1.072 | H | Cl | S | $i-C_3H_7$ | |
| 1.073 | H | Cl | S | $n-C_4H_9$ | |
| 1.074 | H | Cl | S | $CH_2-CH=CH_2$ | |
| 1.075 | H | Cl | S | $CH_2-C\equiv CH$ | |
| 1.076 | H | Br | S | $CH_3$ | |
| 1.077 | H | Br | S | $C_2H_5$ | |
| 1.078 | H | Br | S | $n-C_3H_7$ | |
| 1.079 | H | Br | S | $i-C_3H_7$ | |
| 1.080 | H | Br | S | $n-C_4H_9$ | |
| 1.081 | H | Br | S | $CH_2-CH=CH_2$ | |
| 1.082 | H | Br | S | $CH_2-C\equiv CH$ | |
| 1.083 | F | Cl | S | $CH_3$ | |
| 1.084 | F | Cl | S | $C_2H_5$ | |
| 1.085 | F | Cl | S | $n-C_3H_7$ | |
| 1.086 | F | Cl | S | $i-C_3H_7$ | |
| 1.087 | F | Cl | S | $n-C_4H_9$ | |
| 1.088 | F | Cl | S | $i-C_4H_9$ | |
| 1.089 | F | Cl | S | $s-C_4H_9$ | |
| 1.090 | F | Cl | S | $t-C_4H_9$ | |
| 1.091 | F | Cl | S | $n-C_5H_{11}$ | |
| 1.092 | F | Cl | S | cyclopentyl | |
| 1.093 | F | Cl | S | cyclohexyl | |
| 1.094 | F | Cl | S | $CH_2-CH=CH_2$ | |
| 1.095 | F | Cl | S | $CH_2-C(CH_3)=CH_2$ | |
| 1.096 | F | Cl | S | $CH_2-CH=CH-CH_3$ | |
| 1.097 | F | Cl | S | $CH_2-C\equiv CH$ | |
| 1.098 | F | Br | S | $CH_3$ | |
| 1.099 | F | Br | S | $C_2H_5$ | |
| 1.100 | F | Br | S | $n-C_3H_7$ | |
| 1.101 | F | Br | S | $i-C_3H_7$ | |
| 1.102 | F | Br | S | $n-C_4H_9$ | |
| 1.103 | F | Br | S | $i-C_4H_9$ | |
| 1.104 | F | Br | S | $s-C_4H_9$ | |
| 1.105 | F | Br | S | $t-C_4H_9$ | |
| 1.106 | F | Br | S | $n-C_5H_{11}$ | |
| 1.107 | F | Br | S | cyclopentyl | |
| 1.108 | F | Br | S | cyclohexyl | |
| 1.109 | F | Br | S | $CH_2-CH=CH_2$ | |
| 1.110 | F | Br | S | $CH_2-C(CH_3)=CH_2$ | |
| 1.111 | F | Br | S | $CH_2-CH=CH-CH_3$ | |
| 1.112 | F | Br | S | $CH_2-C\equiv CH$ | |

Example 2

Formulation Examples

Example 2.1:

Formulation examples for active ingredients of the formula I (%=percent by weight)

| (a) emulsifiable concentrates | (a) | (b) | (c) |
|---|---|---|---|
| active ingredient according to Preparation Example 1 | 20% | 40% | 50% |
| Ca dodecylbenzenesulphonate | 5% | 8% | 5.8% |
| castor oil polyethylene glycol ether (36 mol EO) | 5% | — | — |
| tributylphenoyl polyethylene glycol ether (30 mol EO) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) solutions | (a) | (b) | (c) |
|---|---|---|---|
| active ingredient according to Preparation Example 1 | 80% | 10% | 5% |
| ethylene glycol monomethyl ether | 20% | — | — |
| polyethylene glycol MW 400 | — | 70% | — |
| N-methyl-2-pyrrolidone | — | 20% | 5% |
| epoxidised coconut oil | — | — | 90% |

The solutions are suitable for use in the form of extremely fine droplets.

| (c) granulates | (a) | (b) |
|---|---|---|
| active ingredient according to Preparation Example 1 | 5% | 10% |
| kaolin | 94% | — |

| (c) granulates | (a) | (b) |
|---|---|---|
| highly disperse silicic acid | 1% | — |
| attapulgite | — | 90% |

The active ingredient is dissolved and sprayed onto the carrier, and the solvent is subsequently evaporated off in vacuo.

| (d) dust | (a) | (b) | (c) |
|---|---|---|---|
| active ingredient according to Preparation Example 1 | 2% | 5% | 8% |
| highly disperse silicic acid | 1% | 5% | 5% |
| talcum | 97% | — | — |
| kaolin | — | 90% | 87% |

A ready-for-use dust is obtained by intimately mixing the carriers with the active ingredient.

| (e) wettable powders | (a) | (b) |
|---|---|---|
| active ingredient according to Preparation Example 1 | 20% | 60% |
| Na ligninsulphonate | 5% | 5% |
| Na lauryl sulphate | — | 6% |
| octylphenol polyethylene glycol ether (7-8 mol EO) | — | 2% |
| highly disperse silicic acid | 5% | 27% |
| kaolin | 70% | — |

The active ingredient is thoroughly mixed with the adjuvants and thoroughly ground in a suitable mill. Wettable powders are obtained which can be diluted with water to form a suspension of any desired concentration.

| (f) extruder granulate | |
|---|---|
| active ingredient according to Preparation Example 1 | 10% |
| Na ligninsulphonate | 2% |
| carboxymethylcellulose | 1% |
| kaolin | 87% |

The active ingredient is mixed with the adjuvants, and the mixture is ground and moistened with water. This mixture is extruded and then dried in a stream of air.

| (g) coated granules | |
|---|---|
| active ingredient according to Preparation Example 1 | 3% |
| polyethylene glycol (MW 200) | 3% |
| kaolin | 94% |

In a mixer, the finely ground active ingredient is applied uniformly to the kaolin, which has been moistened with polyethylene glycol. In this manner, dust-free coated granules are obtained.

| (h) suspension concentrate | |
|---|---|
| active ingredient according to Preparation Example 1 | 40% |
| ethylene glycol | 10% |
| nonylphenolpolyethylene glycol ether (15 mol EO) | 6% |
| Na ligninsulphonate | 10% |
| carboxymethylcellulose | 1% |
| 37% strength aqueous formaldehyde solution | 0.2% |
| silicone oil in the form of a 75% strength aqueous emulsion | 0.8% |
| water | 32% |

The finely ground active ingredient is intimately mixed with the adjuvants. There is thus obtained a suspension concentrate from which suspensions of any desired concentration can be prepared by dilution with water.

EXAMPLE 3

Biological Examples

EXAMPLE 3.1:

Pre-emergence herbicidal action

In a greenhouse, immediately after the test plants have been sown in sowing trays, the surface of the soil is treated with an aqueous dispersion of the active ingredients, obtained from a 25% strength emulsifiable concentrate. Concentrations of 4 kg of active ingredient/hectare are used. The sowing trays are kept in the greenhouse at 22°–25° C. and 50–70% relative humidity and the test is evaluated after 3 weeks.

In this test the compounds according to Preparation Example 1 exhibit a strong herbicidal action.

EXAMPLE 3.2:

Post-emergence herbicidal action (contact herbicide)

A number of weeds, both monocotyledonous and dicotyledonous, were sprayed after emergence (at the 4 to 6 leaf stage) with an aqueous active ingredient dispersion at a dosage of 4 kg of active ingredient per hectare and the plants were kept at 24°–26° C. and 45–60% relative humidity. 15 days after the treatment the test is evaluated. In this test too, the compounds according to Preparation Example 1 exhibit a strong to very strong herbicidal action.

EXAMPLE 3.3:

Selectivity with respect to cereals in pre-emergence

In a test arrangement in accordance with Example 3.1, compound A (according to Example 1.031) and compound B known from EP-A 61741, of the formulae:

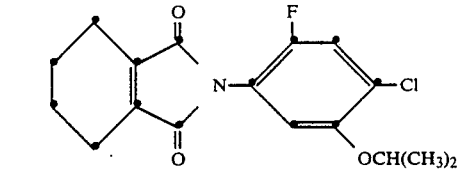

(compound according to Example 1.031)

are compared with one another at application rates of 1000, 500 and 250 g/ha.

The condition of the plants is evaluated in accordance with the following evaluation scale:
1 plant has withered or has not germinated
2–8 decreasing degrees of damage
9 no damage, the plant is developing like untreated control plants The following herbicidal actions are found for A and B (Column 1:1000 g/ha, Column 2:500 g/ha, Column 3:250 g/ha):

| Compound | A Column | | | B Column | | |
|---|---|---|---|---|---|---|
| | 1 | 2 | 3 | 1 | 2 | 3 |
| wheat | 8 | 9 | 9 | 7 | 7 | 8 |
| barley | 7 | 8 | 9 | 2 | 6 | 7 |
| Sinapis | 1 | 1 | 1 | 1 | 1 | 1 |
| Capsella | 1 | 1 | 1 | 1 | 1 | 1 |
| Chenopodium album | 1 | 1 | 1 | 1 | 1 | 1 |
| Chrysanthemum | 1 | 1 | 1 | 1 | 1 | 1 |
| Galium aparine | 1 | 2 | 2 | 1 | 3 | 7 |
| Papaver | 1 | 1 | 1 | 1 | 1 | 1 |
| Poa annua | 1 | 1 | 1 | 1 | 1 | 1 |
| Polygonum | 1 | 1 | 1 | 1 | 1 | 1 |
| Rumex | 1 | 1 | 1 | 1 | 1 | 1 |
| Stellaria | 1 | 1 | 1 | 1 | 1 | 1 |
| Veronica persica | 1 | 1 | 1 | 1 | 1 | 1 |
| Viola tricolor | 1 | 1 | 1 | 1 | 1 | 1 |

EXAMPLE 3.4:

Selectivity with respect to cereals in post-emergence

In a test arrangement in accordance with Example 3.2, compound A (according to Example 1.031) and compound B known from EP-A No. 61741, of the formulae:

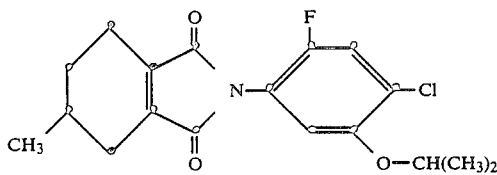

(compound according to Example 1.031)

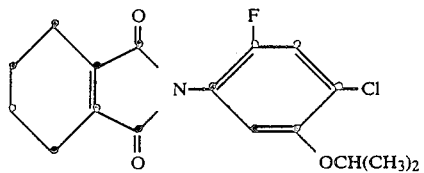

are compared with one another at application rates of 500, 250 and 125 g/ha. The results are evaluated in accordance with the scheme given in Example 3.3.

The following herbicidal actions are found for A and B (Column 1:500 g/ha, Column 2:250 g/ha, Column 3:125 g/ha):

| Compound | A Column | | | B Column | | |
|---|---|---|---|---|---|---|
| | 1 | 2 | 3 | 1 | 2 | 3 |
| wheat | 9 | 9 | 9 | 5 | 7 | 7 |
| barley | 9 | 9 | 9 | 5 | 6 | 6 |
| Chenopodium album | 1 | 1 | 2 | 1 | 1 | 3 |
| Chrysanthemum | 1 | 1 | 1 | 1 | 2 | 2 |
| Galium aparine | 1 | 2 | 2 | 2 | 2 | 2 |
| Papaver | 1 | 1 | 1 | 1 | 1 | 1 |
| Polygonum | 1 | 1 | 2 | 1 | 1 | 1 |
| Rumex | 1 | 1 | 1 | 1 | 1 | 2 |
| Stellaria | 2 | 2 | 2 | 3 | 4 | 5 |
| Veronica persica | 1 | 1 | 1 | 1 | 1 | 1 |
| Viola tricolor | 1 | 1 | 2 | 2 | 2 | 3 |

EXAMPLE 3.5:

Herbicidal action for paddy

The water weeds *Echinochloa crus galli* and *Monocharia vag.* are sown in plastics beakers (60 cm² surface area, 500 ml volume). After sowing, the beakers are filled with water up to the surface of the soil. 3 days after sowing the water level is increased to slightly above (3–5 mm) the surface of the soil. An aqueous emulsion of the test substances is applied 3 days after sowing by being sprayed onto the vessels at an application rate of from 0.5 to 4 kg of active ingredient per hectare. The plant beakers are then placed in a greenhouse under optimum conditions for the growth of the rice weeds, that is to say at from 25° to 30° C. and high humidity. The tests are evaluated 3 weeks after application. The compounds according to Preparation Example 1 damage the weeds but do not damage the rice.

We claim:
1. A compound of the formula

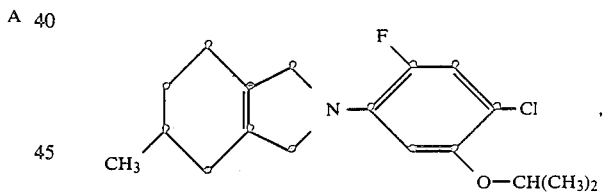

2. A herbicidal composition, characterized in that, in addition to carriers and/or other adjuvants, it contains as active ingredient the compound according to claim 1.

3. A method for controlling weeds, characterized in that the weeds or their growing area are(is) treated with a herbicidally active amount of the compound according to claim 1.

4. A method according to claim 3 for the selective control of weeds.

5. A method according to claim 4, for the selective control of weeds in soya, cotton, oats, rye, millet, maize, wheat, barley and rice.

* * * * *

UNITED STATES PATENT AND TRADEMARK OFFICE
CERTIFICATE OF CORRECTION

PATENT NO. : 4,990,176

DATED : 2/5/91

INVENTOR(S) : Bohner et al.

It is certified that error appears in the above-identified patent and that said Letters Patent is hereby corrected as shown below:

On the cover page of the Patent item 21, should read:

-- (21) Appl. No.: 264,285--.

Signed and Sealed this

First Day of September, 1992

Attest:

DOUGLAS B. COMER

*Attesting Officer*      Acting Commissioner of Patents and Trademarks